United States Patent [19]

Babb

[11] 4,411,792
[45] Oct. 25, 1983

[54] LYMPH FILTRATION SYSTEM

[75] Inventor: Albert L. Babb, Seattle, Wash.

[73] Assignee: Trimedyne, Inc., Arlington Heights, Ill.

[21] Appl. No.: 291,175

[22] Filed: Aug. 10, 1981

[51] Int. Cl.³ .................... B01D 31/00; B01D 13/00
[52] U.S. Cl. .................... 210/651; 210/195.2; 210/411; 210/433.2; 604/5; 604/30
[58] Field of Search .................... 128/214 R, 1 R; 210/195.2, 456, 411, 412, 433.2, 927, 651; 604/5, 30

[56] References Cited

U.S. PATENT DOCUMENTS

| | | | |
|---|---|---|---|
| 3,429,444 | 2/1969 | Spiegel et al. | 210/411 X |
| 3,511,238 | 5/1970 | Von Wrangell | 128/214 R |
| 3,556,302 | 1/1971 | Agranat | 210/456 X |
| 3,579,441 | 5/1971 | Brown | 210/23 |
| 3,705,100 | 12/1972 | Blatt et al. | 210/23 |
| 4,002,567 | 1/1977 | Konno et al. | 210/333 R |
| 4,083,786 | 4/1978 | Tsuda et al. | 210/321 P |
| 4,086,924 | 5/1978 | Latham, Jr. | 128/214 R |
| 4,191,182 | 3/1980 | Popovich et al. | 210/195.2 X |
| 4,243,532 | 1/1981 | Tsuda et al. | 210/196 |

FOREIGN PATENT DOCUMENTS 51-197609 3/1976 Japan .................. 210/411

OTHER PUBLICATIONS

Solomon et al., "Continuous Flow Membrane Filtration of Plasma from Whole Blood", from Trans. Am. Soc. Artif. Inter. Organs, vol. XXIV, 1978, pp. 21–26.

Primary Examiner—Frank A. Spear, Jr.

[57] ABSTRACT

A lymphapheresis or lymph filtration system is disclosed for removing lymph from a patient, separating the lymph into a liquid fraction and a cellular component fraction and returning the liquid fraction to the patient. The system includes an input pump to pump lymph from the patient into a filtration cell having a membrane which filters the lymph into fractions. The liquid fraction is removed from the cell by a reversible pump and is returned to the patient. As the membrane becomes plugged the reversible pump is reversed to backflush the membrane to return it to a high filtration rate. The cellular component fraction which includes lymphocytes is disposed of.

27 Claims, 2 Drawing Figures

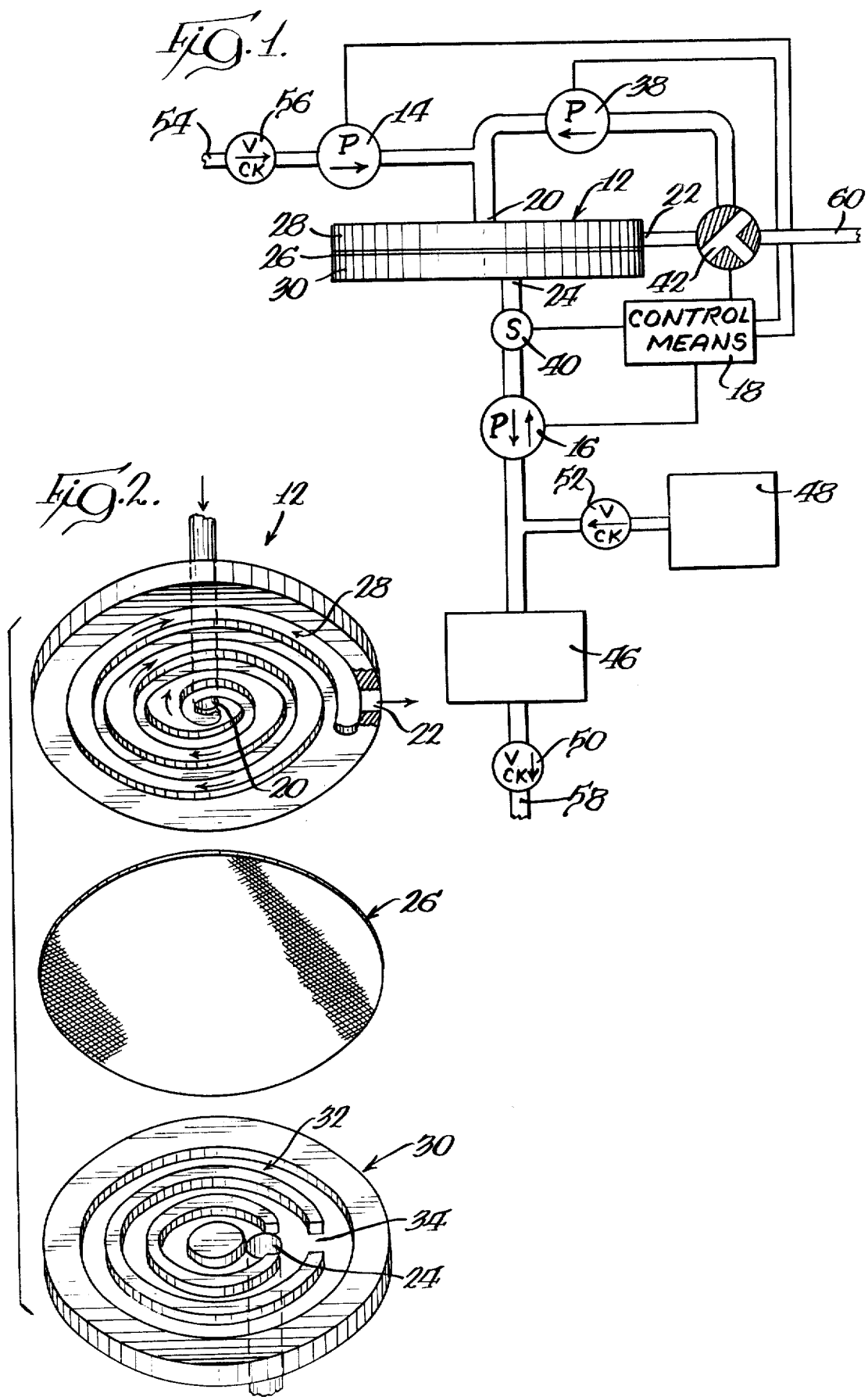

LYMPH FILTRATION SYSTEM

TECHNICAL FIELD

This invention relates to systems for filtering lymph, or lymphapheresis, and more particularly to systems which remove lymph from a patient, separate it into a cellular component fraction and a liquid fraction and return the liquid fraction to the patient.

BACKGROUND OF THE INVENTION

Lymph is a generally transparent, slightly yellow fluid substance which comprises a clear liquid and cellular components, such as lymphocytes. In recent years, it has been shown that lymphocyte depletion by thoracic duct drainage has immumosuppressive effects which can be useful in preventing rejection of transplanted tissue and the treatment of auto-immune diseases.

In the past, lymphocyte depletion has been accomplished by removing lymph from a patient and replacing that lymph with a solution of 5% albumin in saline (plasmetin) mixed with fresh plasma. Lymph has also been withdrawn from a patient, frozen and held for 6 to 7 days to kill the lymphocytes, and then thawed and returned to the patient. Another method removes lymph from a patient, centrifuges it and then returns the liquid fraction to the patient, discarding the cellular component fraction. However this takes extensive equipment and is difficult to use for continuous separation. Filtering is effective for continuous separation except that the filter eventually becomes clogged or plugged with cells and debris.

Various designs have been proposed for devices to separate a body fluid such as blood into a cellular component fraction and a liquid fraction. Illustrative of such devices are U.S. Pat. No. 4,111,199 to Djerassi, U.S. Pat. Nos. 4,059,108 and 4,086,924 to Latham, U.S. Pat. No. 4,083,786 to Tsuda et al., U.S. Pat. No. 3,705,100 to Blatt et al. and U.S. Pat. No. 4,191,182 to Popovich et al. However, none of these devices are directed to a treatment of lymph. The devices to Popovich, Djerassi, Latham and Blatt all are designed to return the cellular component fraction to the patient and are not suitable for lymphocyte depletion which disposes of the cellular components. None of these devices disclose a means to maintain a filter element in an operating condition without becoming plugged through continuous use.

Accordingly, it is desirable to provide a system to perform lymphapheresis by separating the lymph into a cellular component fraction and a liquid fraction and then returning the liquid fraction to the patient. It is also desirable to have a system that includes a means for maintaining a filter in an unplugged operating condition even during prolonged use. The system of the present invention meets these desires.

SUMMARY OF THE INVENTION

The present invention is a lymphapheresis or lymph filtration system for separating lymph into a liquid fraction and a cellular component fraction. The cellular component fraction generally contains cells such as lymphocytes and some liquid while the liquid fraction is the clear fluid that remains after the cellular components have been removed from lymph.

The present system operates by removing lymph from a patient from a location such as the thoracic duct. The lymph may be stored first or transported directly to the system. An input pump delivers the lymph into the inlet of a filtration cell which is divided into a filtering chamber and a filtrate chamber by a membrane filter. The lymph enters through the inlet and preferably passes through a spiral flow path substantially planar with the membrane filter while the liquid fraction passes through the membrane filter. The portion not passing through the membrane filter, the cellular component fraction which contains lymphocytes, other cells and some liquid, then exits through a cellular component outlet. The membrane filter can be made disposable when it becomes plugged.

Preferably, the system is provided with a recirculation loop in fluid communication between the cellular component outlet and the inlet of the filtration cell. This recirculation loop includes a recirculation pumping means which pumps fluid from the cellular component outlet back to the inlet. The loop operates to maintain a fluid velocity through the filtering chamber and across the surface of the membrane filter that is greater than the velocity of the lymph stream withdrawn from the patient. This provides a relatively high speed current across the membrane surface having a shear rate of about 2000 sec$^{-1}$ to about 2500 sec$^{-1}$, which is instrumental in minimizing the plugging up of the pores in the membrane filter by the cellular components present.

The liquid fraction passes through the membrane filter, enters the filtrate chamber, and exits through a filtrate outlet. A reversible filtrate pump is placed in fluid communication with the filtrate outlet. The operation of the filtrate pump is regulated by a control means. When the filtrate pump is in its operating mode, it pumps the liquid fraction from the filtrate chamber to storage or returns the liquid fraction to the patient e.g., to the patient's thoracic direct downstream from the point where the patient's lymph is being withdrawn. When the filtrate pump is in its backflush mode, it pumps fluid into the filtrate chamber to produce a positive transmembrane pressure from the filtrate chamber to the filter chamber to backflush the membrane filter. This unplugs the membrane filter and allows the filter to maintain a high rate of lymph separation over an extended time period. Without this periodic backflushing the filtering rate of the membrane filter would steadily decline as it became progressively plugged.

The backflushing fluid may be a previously filtered liquid fraction or may be another liquid such as sterile saline solution. The backflushing fluid can be stored in a reservoir in fluid communication with the filtrate pump, if desired.

Numerous other advantages and features of the present invention will become readily apparent from the following detailed description of the invention, the accompanying example, and the appended claims.

BRIEF DESCRIPTION OF THE DRAWING

FIG. 1 shows a schematic representation of a lymph filtration system of the present invention including a filtration cell, pumps, valves and reservoirs.

FIG. 2 is an enlarged, exploded perspective view of the filtration cell showing its internal structure.

DESCRIPTION OF THE PREFERRED EMBODIMENT

While this invention is susceptible to embodiment in many different forms, there is shown in the drawing and will be described in detail, one specific embodiment of the invention. It should be understood, however, that the present disclosure is to be considered as an exemplification of the principles of the invention and is not intended to limit the invention to the embodiment illustrated.

The precise shapes and sizes of the components described are not essential to the invention unless otherwise indicated. The system of the present invention has certain conventional pumping means and valve mechanisms, the details of which, though not fully illustrated or described, will be apparent to those having skill in the art and the understanding of the necessary function of such mechanisms.

Referring to the drawings, the lymph filtration of the invention generally comprises a filtration cell 12, an input pumping means such as input pump 14, a reversible filtrate pumping means such as filtrate pump 16 and control means 18 for regulating the operation of the filtrate pump.

The filtration cell 12 has an inlet 20 in fluid communication with the input pump 14, a cellular component outlet 22, and a filtrate outlet 24 in fluid communication with the filtrate pump 16. The filtrate cell also has a membrane or membrane filter 26 which divides the filtration cell into a filtering chamber 28 and a filtrate chamber 30. The inlet 20 and the cellular component outlet 22 are in fluid communication with the filtering chamber 28 and the filtrate outlet 24 is in fluid communication with the filtrate chamber 30.

The filtrate pump 16 is a reversible pump which, when in its operating mode, pumps liquid fraction from the filtrate chamber 30. The filtrate pump 16 may be a constant volume pump. When the filtrate pump 16 is in its backflush mode, it pumps fluid into the filtrate chamber 30 to produce a positive transmembrane pressure from the filtrate chamber to the filtering chamber 28 to backflush the membrane. Preferably the transmembrane pressure in the backflush mode is about 150 to about 350 mmHg. As the membrane filter 26 becomes plugged by cellular components or other debris, this occassional backflushing unplugs the membrane filter to return to a higher rate of filtration.

The filtering chamber 28 preferably has a spiral flow path channel between the inlet 20 and the cellular component outlet 22 as can best be seen in FIG. 2. The spiral flow path is substantially planar with the membrane filter 26. The filtering chamber 28 preferably has an effective height as measured perpendicular to the membrane filter 26 from about 0.1 millimeters to about 1.0 millimeters. That is, the liquid column passing over the membrane filter 26 has a height of about 0.1 to about 1.0 millimeters. Typically, the channel has a width of about 0.1 to about 0.2 millimeter. The spiral flow path directs the flow of lymph over the surface of the membrane filter 26 at a relatively high average fluid velocity of about 20 to about 30 centimeters per second to provide a shear rate of about 1600 sec$^{-1}$ to about 2400 sec$^{-1}$.

The wall shear rate (Sw) can be calculated according to $Sw = 6V/h = 6Q/wh^2$ where V is the average fluid velocity, h is the channel or chamber height, Q is the volumetric flow rate and w is the width of the flow channel. Thus, for a chamber height of 0.75 millimeters and a typical average fluid velocity of about 20 centimeters per second the wall shear rate is 1600 sec$^{-1}$. Preferably the shear rate should be from about 500 to about 2500 sec$^{-1}$. These high shear rates help minimize the amount of cellular components and other debris that obstructs the membrane filter as filtration is carried out.

The membrane filter 26 preferably has an effective pore size of about 0.1 microns to about 1.0 microns. A Nuclepore 0.6 micron membrane having a nominal thickness of 10 microns and commercially available from Nuclepore, Corp. of Pleasanton, CA is suitable.

Similarly, the filtrate chamber may be defined by a series of concentric grooves 32 interconnected by a flow channel or slot 34, the grooves being generally coplanar with the membrane filter 26, substantially in registry with filtering chamber 28 on the opposite side of membrane filter 26, and in fluid communication with the filtrate outlet 24. This provides backing for the filter membrane 26 while providing a pathway for the liquid fraction to flow out filtrate outlet 24.

To further increase the shear rate of the lymph as it passes over the membrane filter 26, the system is preferably provided with a recirculation loop 36 and a recirculation pumping means or pump 38 which draws fluid from the cellular component outlet 22 and reintroduces it into the inlet 20. Thus, there is a continuous flow through the filtering chamber 28 and over the surface of the membrane filter 26 to minimize the amount of cellular components and debris obstructing the membrane filter. The recirculation pump 38 can be combined with the input pump 14, if desired.

The control means 18 regulates the operation of the filtrate pump 16. The control means 18 may be a timer which on a regular cycle, such as every five minutes, puts the filtrate pump in its backflush mode for a predetermined time period. Alternatively, the control means 18 may be operably associated with a sensing means 40, e.g. a hydraulic sensor, which in turn is associated with the filtration cell 12. Depending on the information received from the sensing means, the control means determines whether the membrane filter 26 should be backflushed. The sensing means 40 may be a pressure sensor, a volumetric flow rate sensor, or any other sensor that provides information about the operation of the filtration cell 12 and/or the permeability of the membrane filter to the liquid fraction.

As an illustration, when the sensing means 40 is a pressure sensor, when the pressure from the filtrate outlet 24 drops to a certain point, the control means directs the filtrate pump 16 to enter the backflush mode. Alternatively, when the sensing means 40 is a volumetric flow rate sensor, when the rate of liquid fraction leaving the filtrate outlet 24 drops below a certain point, the control means 18 directs the filtrate pump 16 to enter the backflush mode. Additionally, the control means 18 may be operably associated with the input pump 14, the recirculation pump 38 and an exit valve 42 to monitor and control operation of the system.

Preferably, the lymph filtration system is provided with at least one liquid reservoir such as reservoir 46 or reservoir 48. Either or both reservoirs may be present. In the case when reservoir 46 is the only reservoir present, reservoir 46 retains an aliquot of the filtered liquid fraction for use to backflush the filtration cell 12. Outlet check valve 50 prevents liquid fraction from being drawn from the patient.

Alternatively, reservoir 48, also known as a backflush fluid source may be the only reservoir present. Between the backflush fluid source 48 and the filtrate pump 16 is a backflush check valve 52. In this configuration liquid fraction is pumped directly from the filtration cell to the patient or to a collection container. When the filtrate pump 16 enters into the backflush mode, backflush fluid such as sterile saline solution is drawn from the backflush fluid source 48 and pumped into the filtrate chamber 30 to backflush the filtration cell 12. Outlet checkvalve 50 prevents liquid fraction from being drawn from the patient during backflush and backflush checkvalve 52 prevents liquid fraction from entering the backflush fluid source 48 during operation. By using a fluid such as sterile saline to backflush the filtration cell 12, a minimum amount of liquid fraction is lost that otherwise could be delivered to the patient or retained for subsequent use.

In operation, input fluid line 54 having an input check valve 56 is put in fluid communication with the patient from whom lymph is to be withdrawn. The patient is protected by input check valve 56. Lymph is drawn into the system by input pump 14 and introduced into the filtering chamber 28 of the filtration cell 12. Liquid fraction passes through the membrane filter 26 and is drawn out of the filtrate chamber 30 by filtrate pump 16. The transmembrane pressure from the filtering chamber 28 to the filtrate chamber 30 is preferably about 150 mmHg to about 20 mmHg. The hydraulic properties of the filtration cell 12 are sensed by sensing means 40 which regulates control means 18. The liquid fraction passes through filtrate pump 16 through reservoir 46, through outlet check valve 50 and to the patient through outlet line 58.

Liquid fraction and cellular components that do not pass through the membrane filter 26 exit through the cellular component outlet 22 to exit valve 42. In operation, exit valve 42 directs fluid to the recirculation loop 36 and disposal line 60 either separately or together. Part of the fluid is drawn into the recirculation loop 36 by recirculation pump 38 and pumped through the inlet into the filtration cell. As discussed above, this increases the shear rate across the face of the membrane, thus avoiding plugging of the membrane filter 26.

When either a predetermined time limit has passed or sensor 40 indicates the appropriate condition, control means 18 directs the filtrate pump 16 to reverse, sending it into a backflush mode. Backflush fluid such as sterile saline is then drawn from backflush fluid source 48 through backflush checkvalve 52 and pumped into filtrate chamber 30 to backflush the membrane filter 26.

During the backflush mode, exit valve 42 may be aligned to connect the cellular component outlet to only the disposal line 60. Additionally, the control means may also deactivate the input pump 14 and the circulating pump 38. Thus, any debris or cellular components which are liberated from the surface of the membrane filter 26 are then disposed out through the disposal line 60.

By way of example, 20 milliliters per minute of lymph is pumped in through input fluid line 54. The lymph is pumped by input pump 14 and passed in spiral stream over one side of the membrane filter 26. Input pump 14 and filtrate pump 16 introduce a positive pressure is chamber 28 and provide a driving force for liquid to pass through the membrane filter 26 while lymph is circulated through the chamber 28 at a rate of about 220 milliliters per minute and a linear velocity of about 60 feet per minute across the surface of membrane 26. About 16 milliliters per minute of liquid fraction passes through the membrane filter 26 and is collected by filtrate pump 16 which is periodically reversed to introduce a negative transmembrane pressure to backflush the membrane filter. About 4 milliliters per minute of a fraction enriched in cellular components is discarded through disposal line 60.

The foregoing specification is intended as illustrative and is not to be taken as limiting. Still other variations within the spirit and scope of this invention are possible and will readily present themselves to those skilled in the art.

What is claimed is:

1. A lymph filtration system for separating lymph into a liquid fraction and a cellular component fraction, the system comprising:
    (a) a filtration cell having an inlet, a cellular component outlet and a filtrate outlet, the filtration cell also having a membrane filter dividing the cell into filtering and filtrate members, the inlet and cellular component outlet in fluid communication with the filtering chamber, the filtrate outlet in fluid communication with the filtrate chamber;
    (b) an input pumping means for delivering lymph to the inlet of the filtration cell;
    (c) an inlet check valve between a patient and the input pumping means;
    (d) a reversible filtrate pumping means in fluid communication with the filtrate outlet for pumping fluid to and from the filtrate chamber, the filtrate pumping means when in an operating mode to pump liquid fraction from the filtrate chamber, and when in a backflush mode, to pump a fluid into the filtrate chamber to produce a positive transmembrane pressure from the filtrate chamber to the filtering chamber to backflush the membrane filter; and
    (e) control means for controlling the operation of the filtrate pumping means.

2. The lymph filtration system of claim 1 wherein the membrane filter has an effective pore size of about 0.1 to about 1.0 microns.

3. The lymph filtration system of claim 1 wherein the filtering chamber is further defined by a spiral flow path between the inlet and the cellular component outlet, the spiral flow path being substantially planar with the membrane.

4. The lymph filtration system of claim 1 wherein the filtrate chamber defines a series of concentric grooves interconnected by a slot, the grooves being generally coplanar with the membrane and in fluid communication with the filtrate outlet.

5. The lymph filtration system of claim 1 including a recirculation loop in fluid communication between the cellular component outlet and the inlet of the filtration cell, the recirculation loop having a recirculation pumping means for pumping fluid from the cellular component outlet to the inlet to increase fluid flow through the filtering chamber.

6. The lymph filtration system of claim 1 including a hydraulic sensing means operably associated with the filtration cell for providing information to the control means.

7. A lymph filtration system for separating lymph into a liquid fraction and a cellular component fraction, the system comprising:
    (a) a filtration cell having an inlet, a cellular component outlet and a filtrate outlet, the filtration cell also having a membrane filter dividing the cell into filtering and filtrate chambers, the inlet and cellular component outlet in fluid communication with the filtering chamber, the filtrate outlet in fluid communication with the filtrate chamber;
    (b) an input pumping means for delivering lymph to the inlet of the filtration cell;

(c) a reversible filtrate pumping means in fluid communication with the filtrate outlet for pumping fluid to and from the filtrate chamber, the filtrate pumping means when in an operating mode to pump liquid fraction from the filtrate chamber, and when in a backflush mode, to pump a fluid into the filtrate chamber to produce a positive transmembrane pressure from the filtrate chamber to the filtering chamber to backflush the membrane filter;

(d) control means for controlling the operation of the filtrate pumping means;

(e) a reservoir in fluid communication between the filtrate pumping means and a patient; and (f) an outlet check valve between the reservoir and the patient;

the filtrate pumping means, when in the backflush mode, pumping liquid fraction from the reservoir into the filtrate chamber.

8. A lymph filtration system for separating lymph into a liquid fraction and a cellular component fraction, the system comprising:

(a) a filtration cell having an inlet, a cellular component outlet and a filtrate outlet, the filtration cell also having a membrane filter dividing the cell into filtering and filtrate chambers, the inlet and cellular component outlet in fluid communication with the filtering chamber, the filtrate outlet in fluid communication with the filtrate chamber;

(b) an input pumping means for delivering lymph to the inlet of the filtration cell;

(c) a reversible filtrate pumping means in fluid communication with the filtrate outlet for pumping fluid to and from the filtrate chamber, the filtrate pumping means when in an operating mode to pump liquid fraction from the filtrate chamber, and when in a backflush mode, to pump a fluid into the filtrate chamber to produce a positive transmembrane pressure from the filtrate chamber to the filtering chamber to backflush the membrane filter;

(d) control means for controlling the operation of the filtrate pumping means;

(e) an outlet check valve between the filtrate pumping means and the patient;

(f) a backflush fluid source in fluid communication with the filtrate pumping means between the filtrate pumping means and the outlet check valve; and (g) a backflush check valve between the backflush fluid source and the filtrate pumping means such that when the filtrate pumping means is in the operating mode, liquid fraction is pumped from the filtrate chamber to the patient and when the filtrate pumping means is in the backflush mode, backflushing fluid is pumped from the backflush fluid source into the filtrate chamber.

9. A lymph filtration system for separating lymph into a liquid fraction and a cellular component fraction, the system comprising:

(a) a filtration cell having an inlet, a cellular component outlet and a filtrate outlet, the filtration cell also having a membrane filter dividing the cell into a filtering chamber and a filtrate chamber, the inlet and cellular component outlet in fluid communication with the filtering chamber and the filtrate outlet in fluid communication with the filtrate chamber, the filtrate chamber defining a spiral flow path between the inlet and the cellular component outlet, the spiral flow path being substantially coplanar with the membrane filter;

(b) an input pumping means for pumping lymph from a patient to the inlet of the filtration cell;

(c) an inlet check valve between the patient and the input pumping means;

(d) a hydraulic sensing means operably associated with the filtrate outlet;

(e) a reversible filtrate pumping means in fluid communication with the filtrate outlet for pumping fluid to and from the filtrate chamber, the filtrate pumping means when in the operating mode to pump liquid fraction from the filtrate chamber to the patient, and when in a backflush mode, to pump fluid into the filtrate chamber to produce a positive transmembrane pressure from the filtrate chamber to the filtering chamber to backflush the membrane filter;

(f) a control means operably associated with the hydraulic sensor for regulating the outlet pumping means; and (g) a reservoir in fluid communication with the filtrate pumping means.

10. The lymph filtration system of 9 wherein the membrane filter has an effective pore size from about 0.1 to about 1.0 microns.

11. The lymph filtration system of claim 9 including a recirculation loop in fluid communication between the cellular component outlet and the inlet of the filtration cell, the recirculation loop having a recirculation pumping means for pumping fluid from the cellular component outlet to the inlet to increase fluid flow through the filtering chamber.

12. The lymph filtration system of claim 9 wherein the filtering chamber has a height, measured perpendicular to the membrane filter, from about 0.1 millimeters to about 1.0 millimeters.

13. The lymph filtration system of claim 9 wherein the reservoir is a backflush fluid source having a backflush check valve and including an outlet check valve between the filtrate pumping means and patient such that when the filtrate pumping means is in the operating mode, liquid fraction is pumped from the filtrate chamber to the patient and when in the backflush mode, backflush fluid is pumped from the reservoir into the filtrate chamber.

14. The lymph filtration system of claim 9 wherein the backflush fluid is sterile saline solution.

15. The lymph filtration system of claim 9 wherein the transmembrane pressure from the filtering to filtrate chamber in the operating mode is from about 100 mmHg to about 200 mmHg.

16. The lymph filtration system of claim 9 wherein the transmembrane pressure from the filtrate to the filtering chamber is the backflush mode is from about 150 mmHg to about 350 mmHg.

17. The lymph filtration system of claim 9 wherein the filtrate pumping means is a constant volume pump.

18. The lymph filtration system of claim 9 wherein the lymph passes over the membrane filter with a shear rate of about 500 to about 2500 sec$^{-1}$.

19. A lymph filtration system for removing lymph from a patient, separating the lymph into a liquid fraction and a cellular component fraction and returning the liquid fraction to the patient, the system comprising:

(a) a filtration cell having an inlet, a cellular component outlet and a filtrate outlet, the filtration cell also having a membrane filter dividing the cell into a filtering chamber and a filtrate chamber, the inlet and cellular components outlet in fluid communication with the filtering chamber and the filtrate outlet in fluid communication with the filtrate chamber, the filtrate chamber defining a spiral flow path between the inlet and the cellular component outlet, the spiral flow path being substantially coplanar with the membrane filter;

(b) an input pump for pumping lymph from the patient to the inlet of the filtration cell;

(c) an inlet check valve between the patient and the pump.

(d) a hydraulic sensing means operably associated with the filtrate outlet;

(e) a reversible filtrate pump in fluid communication with the filtrate outlet for pumping fluid to and from the filtrate chamber, the filtrate pump when in the operating mode to pump liquid from the filtrate chamber to the patient, and when in a backflush mode, to pump fluid into the filtrate chamber to produce a positive transmembrane pressure from the filtrate chamber to the filtering chamber to backflush the membrane filter;

(f) a control means operably associated with the hydraulic sensor for controlling the outlet pumping means;

(g) a recirculation loop in fluid communication between the cellular component outlet and the inlet of the filtration cell, the recirculation loop having a recirculation pump to pump fluid from the outlet to the inlet to increase fluid flow through the filtering chamber;

(h) an outlet check valve between the filtrate pump and the patient;

(i) a backflush fluid source in fluid communication with the filtrate pump between the filtrate pump and the outlet check valve; and (j) a backflush check valve between the backflush fluid source and the filtrate pump such that when the filtrate pump is in the operating mode, liquid fraction is pumped from the filtrate chamber to the patient and when the filtrate pump is in the backflush mode, backflushing fluid is pumped from the backflush fluid source into the filtrate chamber.

20. The lymph filtration system of 19 wherein the membrane filter has an effective pore size from about 0.1 to about 1.0 microns.

21. The lymph filtration system of claim 19 wherein the filtrate chamber defines a series of concentric grooves interconnected by a slot, the grooves being generally coplanar with the membrane and in fluid communication with the filtrate outlet.

22. The lymph filtration system of claim 19 wherein the filtering chamber has a height, measured perpendicular to the membrane filter, from about 0.1 millimeters to about 1.0 millimeters.

23. The lymph filtration system of claim 19 wherein the transmembrane pressure from the filtering to filtrate chamber while the filtrate pump is in the operating mode is from about 100 mmHg to about 200 mmHg.

24. The lymph filtration system of claim 19 wherein the transmembrane pressure from the filtrate to the filtering chamber while the filtrate pump is in the backflush mode is from about 150 mmHg to about 350 mmHg.

25. The lymph filtration system of claim 19 wherein the lymph passes over the membrane filter with a shear rate of about 500 to about 2500 sec$^{-1}$.

26. A method for separating lymph into a liquid fraction and a cellular component fraction, the method comprising:

(a) passing a stream of lymph over one side of a membrane filter, the stream having a shear rate in excess of 500 sec$^{-1}$;

(b) introducing a positive transmembrane pressure through the membrane filter;

(c) collecting filtered liquid fraction on the other side of the membrane filter;

(d) periodically introducing a negative transmembrane pressure to backflush the membrane filter; and (e) discarding the cellular component.

27. The method of claim 26 wherein the stream of lymph is constrained to pass in a spiral flow path over the membrane filter.

* * * * *